United States Patent [19]

Briggs

[11] Patent Number: 4,560,881

[45] Date of Patent: Dec. 24, 1985

[54] METHOD AND APPARATUS FOR ENHANCED DETECTION OF ELECTROMAGNETIC SIGNALS

[75] Inventor: Jonathan Briggs, Palo Alto, Calif.

[73] Assignee: Syntex (U.S.A.) Inc., Palo Alto, Calif.

[21] Appl. No.: 589,183

[22] Filed: Mar. 13, 1984

[51] Int. Cl.⁴ .............................................. F21V 9/16
[52] U.S. Cl. .................................................. 250/458.1
[58] Field of Search ...................... 250/458.1, 373, 351

[56] References Cited

U.S. PATENT DOCUMENTS

3,891,853  6/1975  Kremen et al. ................... 250/458.1
4,101,221  7/1978  Schunck et al. ................... 250/351
4,260,890  4/1981  Wright et al. ....................... 250/373
4,421,860 12/1983  Elings et al. ..................... 250/458.1
4,500,204  2/1985  Ogura .............................. 250/458.1

Primary Examiner—Janice A. Howell
Attorney, Agent, or Firm—John A. Dhuey

[57] ABSTRACT

A method and apparatus are described for enhanced detection relative to background radiation, of electromagnetic signals from an emitter of radiation in response to incident radiation. The method and apparatus have particular applicability in the field of particle detection, e.g. fluorescent particle detection.

30 Claims, 6 Drawing Figures

METHOD AND APPARATUS FOR ENHANCED DETECTION OF ELECTROMAGNETIC SIGNALS

BACKGROUND OF THE INVENTION

1. Field of the Invention

The invention is directed to method and apparatus for detecting fluctuations in an electromagnetic signal emitted by a receiver of electromagnetic radiation in response thereto, in the presence of background radiation. In particular, the invention is directed to methods and apparatus utilizing a beam of incident electromagnetic radiation having a spatial distribution of intensity periodically varying in time, and determining the correlation, if any, between the periodicity of the periodically varying spatial distribution of intensity and fluctuations in the measured signal emitted by a receiver of the incident beam. The invention has particular application for detecting the presence of a particle of relatively small dimensions, which elastically or inelastically scatters radiation in response to the incident radiation such as fluorescently labeled cellular particles in physiological fluids, which exhibit relatively low fluorescent fluctuations from the mean fluorescence of a sample, or such as light directly scattered by the particle which is weak compared to the mean scattering of a sample. The methods and apparatus may utilize modulation or periodic change of the spatial pattern of light intensity created by a coherent light source transmitted via a light guide to the sample being analyzed.

2. State of the Art

The use of laser beams and slits to differentiate particles based on their relative size by the correlation of fluorescent fluctuations in a relatively large sample volume is described in: Briggs, et al. "Homogeneous Fluorescent Immunoassay," *Science*, No. 212, 1266–1267 (1981) and Nicoli, et al., "Fluorescence Immunoassay Based on Long-Time Correlations of Number Fluctuations," *Proc. Natl. Acad. Sci. U.S.A.* 77(8), 4904–4908(1980).

The phenomena of light intensity distribution at the output plane of an optical fiber has been described by Rosen et al., "Speckle in Optical Fibers," *Proceedings of the Society of the Photo-Optical Instrumentation Engineers*, Volume 243, 28–33(1980); Kalnitskaya et al., *Opt. Spectrosc. (USSR)*, 44(2), February (1978); Rosen et al., "Frequency Dependence of Modal Noise in Multi-Optical Fibers," *J. Opt. Soc. Am.*, Vol. 70 No. 8 968–976, August (1980); and Kohler et al., "Speckle Reduction in Pulsed-Laser Photographs," *Optics Communications*, Vol. 12 No. 1, 24–28, September (1974). Additionally, U.S. Pat. No. 3,588,217, describes an apparatus for displaying an image of a hologram, utilizing a fiber optic device located to form part of the path of the coherent light illuminating the hologram which is moved at its mid-section while the ends are held rigid as the hologram is viewed to reduce the speckle noise that otherwise occurs in the hologram.

SUMMARY OF THE INVENTION

In a broad aspect, the invention is directed to a method of detecting fluctuations in an electromagnetic signal emitted by a receiver of incident electromagnetic radiation in response thereto, the receiver being suspected of containing an element to be detected or measured, which comprises generating a beam of incident electromagnetic radiation having a spatial distribution of intensity periodically varying with time; irradiating a receiver with the beam; measuring the electromagnetic signal emitted by the receiver upon irradiation; and determining the correlation, if any, between the periodicity of the periodically varying spatial intensity distribution and fluctuations in the measured signal. As used herein and throughout this specification, emmited radiation includes both elastically or inelastically scattered radiation in response to the incident radiation.

Additionally, in a broad aspect the invention is directed to an apparatus for detecting fluctuations in an electromagnetic signal emitted by a receiver of incident electromagnetic radiation in response thereto which comprises means for generating a beam of incident electromagnetic radiation having a spatial distribution of intensity periodically varying in time; means for irradiating a receiver with the beam; means for measuring an electromagnetic signal emitted by the receiver upon irradiation; and means for determining the correlation, if any, between the periodicity of the periodically varying spatial intensity distribution and fluctuation in the measured signal.

The invention provides for a method of determining the presence of an analyte in a sample suspected of containing the analyte which comprises combining the sample with the source of fluorescence; irradiating the combined sample with a source spectrum sufficiently narrow to permit light guided in different modes to interfere and form a speckle pattern at an output plane intersecting a portion of the combined sample; periodically changing the optical path of the guided light to vary the speckle pattern at the output plane during said irradiation; and then determining the correlation, if any, between the measured fluctuations of fluorescent intensity from the combined sample and the periodic change.

In another aspect of the invention, there is provided an apparatus for measuring light from a fluid sample comprising an optical light guide having a probe adapted to extend into the fluid sample, an input light guide and a detector light guide; light irradiating means coupled with the input light guide; light detection means coupled with the detector light guide; modulating means operable on the input light guide to form excitation light means having a time dependent intensity distribution pattern at an output plane of the light guide, such that the light intensity pattern includes contrasting areas of high intensity and low intensity light.

In a presently preferred embodiment the optical light guide is formed from an optical fiber having an input fiber and a detector fiber. Additionally, in a presently preferred embodiment the light irradiating means includes a coherent light source preferably from a laser light source.

DETAILED DESCRIPTION OF THE INVENTION

The present invention is directed to an apparatus and method for measuring or detecting an electromagnetic signal from a receiver of incident electromagnetic radiation, which contains an element that emits an electromagnetic signal responsive to the intensity of the incident radiation, in order to detect the presence of or measure the quantity of such an element in the receiver.

One of the problems often associated with the measurement of a particular electromagnetic signal is the presence of "noise," i.e. unwanted components in the total signal which mask or interfere with the particular signal intended to be measured. Such a problem typically is present in systems designed to measure an electromagnetic signal generated by a receiver of incident electromagnetic radiation, which receiver may contain an element which responds to such radiation by emitting an electromagnetic signal, when the receiver itself independently of the responding element generates extraneous electromagnetic signals upon irradiation. A second factor introducing noise into the measured signal is leakage of the incident electromagnetic radiation into the measurement or detection system, with consequential masking of the desired signal to be measured or detected.

The foregoing problems and difficulties can be understood with greater particularity by reference to copending application Ser. No. 397,285, filed July 12, 1982, which disclosure is incorporated herein by reference. That application describes an optical fiber system for the detection and/or measurement of particles in a sample. As described therein, the characteristics of the optical fiber are utilized to define an effective sample volume in which there is a high probability of having only a few particles in the effective sample volume. Since the intensity of the emitted electromagnetic radiation, e.g. light from a fluorescing particle, can be very low, suitably responsive detection methods and apparatus must be employed to detect the presence of a particle.

The detection of low levels of emitted electromagnetic radiation is further complicated by the presence of "noise" i.e. background radiation, which is transmitted to or generated by the detection apparatus. Such background radiation or noise can arise from the fiber optic components themselves, such as incident radiation leaking from the input optical fibers to the output optical fibers. Additionally, in fluorescing detection systems, background fluorescence, i.e. that fluorescence not attributable to the particle being detected, may be present in the sample. The total electromagnetic signal transmitted to the detector unit, accordingly, is comprised of the emitted radiation from a particle to be detected, if such particle is present in the sample volume, the emitted radiation from any other elements in the sample volume which emit electromagnetic radiation in response to the incident radiation, and electromagnetic radiation generated by the instrumentation, including the fiber optics, which is transmitted to the detection unit.

Much of the instrumentation background radiation generated is a function of the overall or average intensity of the incident electromagnetic radiation which is utilized to irradiate the sample, and is substantially independent of the intensity distribution within the incident beam of electromagnetic radiation. Accordingly, if the incident beam of electromagnetic radiation is supplied with a constant average or mean intensity, notwithstanding the fact that the spatial distribution of intensity within the beam of incident electromagnetic radiation may be periodically changing, variations in instrument background radiation will be substantially zero, and there will be no correlation between that portion of the measured signal and the periodicity of the spatial distribution of intensity of the incident electromagnetic beam.

The other source of noise present in the measured signal, i.e. radiation emitted from uniformly distributed emitters of electromagnetic radiation in the sample, will not be affected by a periodically changing intensity distribution within the incident beam of electromagnetic radiation when the average or mean intensity of the incident bean of radiation is maintained substantially constant. Since the incident beam of radiation will effectively see the same number of emitters at any point in time due to their uniform distribution, the observed background radiation is substantially constant. Thus, when the spatial distribution of intensity of the incident beam of radiation is periodically varied with time, there will be no correlation between that portion of the measured signal generated by the uniformly distributed emitters and the periodicity of the intensity distribution of the incident electromagnetic beam.

In contrast to the foregoing, the emitted radiation resulting from the presence of an element, e.g. particle, to be detected within the receiver, e.g. sample, is subject to the local spatial variations in intensity and periodic changes in spatial distribution of intensity of the incident beam. Accordingly, in response to irradiation by a beam of electromagnetic radiation having a periodically varying spatial intensity distribution and a substantially constant average or mean intensity, the presence of a particle results in correlation between the periodicity of changes in the spatial intensity distribution of the incident beam of electromagnetic radiation and measured fluctuations in the electromagnetic signal emitted from the receiver.

The method and apparatus of the present invention utilize the generation of a beam of incident electromagnetic radiation having a spatial distribution of intensity periodically varying in time while maintaining the average or mean intensity of the beam of incident radiation substantially constant. A suitable beam of incident electromagnetic radiation is provided, for example, by electromagnetic radiation having characteristic interferring wavefronts, so as to create an intensity distribution pattern in the plane of the wave fronts of the radiation in the incident beam. The wave fronts can interfere "constructively" (i.e. at a point of constructive interference the intensity of the electromagnetic beam at the point will be higher than the average or mean intensity over the plane of the wavefronts), or the wavefronts can interfere "destructively" (i.e. at a point of destructive interference the intensity of the electromagnetic beam at the point will be less than the average or mean intensity over the plane of the wavefronts).

Figure 1:
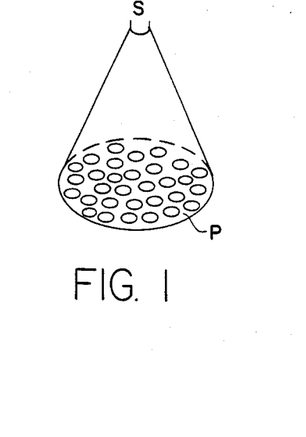
FIG. 1 is an illustration of beam of electromagnetic radiation produced by a source S having an intensity pattern in a plane P intersecting the beam containing substantially discrete high and low intensity areas.

Such an interference pattern at the plane of the wavefronts occurs in what is typically termed a "speckle pattern" and is illustrated in FIG. 1. With high contrast in the speckle pattern, substantially discrete areas of high intensity spots and low intensity spots are defined. Speckle patterns of high contrast are conveniently generated from sources of electromagnetic radiation having a narrow spectrum of wavelengths such as laser light coupled to and transmitted via a multimode optical fiber. The contrast will depend on variations in the indices of refraction of the core and cladding of the optical fiber, the spectral wavelength ranges of the source and the length of the fiber, the contrast being higher for single or near single wavelength sources and with shorter optical fiber lengths. A discussion of contrast as a function of fiber length for several sources and fiber types is found in "Frequency Dependence of Modal Noise in Multimode Optical Fibers," *J. Opt. Soc. Am.*, Vol. 70, No. 8, August 1980, pages 968–976. It is presently preferred to utilize coherent light sources such as a laser light source, particularly those of wavelengths between about 300 to 1000 nanometers.

The spatial distribution of intensity of the beam of incident electromagnetic radiation is varied with time by changing the points of constructive and destructive interference of the wavefronts. Typically, this is accomplished by varying the path length difference of interfering beams of electromagnetic radiation transmitted from the point of generation of the incident beam to the particular point of observation. In an optical fiber, each high intensity spot of radiation is due to a collection of rays which bounce down the fiber and emerge at a particular angle, such that the rays mutually constructively interfere. Each low intensity spot is created in the same manner except that, upon emergence from the fiber at a particular angle, the rays creating the low intensity spot mutually destructively interfere. Accordingly, in the case of a laser generated incident beam and an optical fiber transmitter, the spatial distribution of intensity of the incident beam can be periodically varied with time by providing means for periodically varying the optical path length differences of interfering light beams through the optical fiber. That can be conveniently accomplished by periodically changing the spatial position (e.g. curvature) of a portion of the optical fiber, or by periodically changing the angle of incidence of the laser beam on the input end of the optical fiber (i.e. the angle which one couples light into the optical fiber). Alternately, the spatial distribution of intensity could be periodically varied by subjecting the optical fiber to a periodically changing external field which would change the index of refraction profile within the fiber.

In order to enhance the detection of a selected element in a receiver of the incident radiation, it is desirable to match up or correlate the distance over which the intensity varies, i.e. the size of the areas of high intensity (and areas of low intensity) in the speckle pattern, to the size of the element desired to be detected so as not to detect emitters of electromagnetic radiation which do not have that size or those which are uniformly distributed. Accordingly, it is desirable to create a spatial distribution of intensities having a plurality of substantially discrete areas of differing intensity in a plane perpendicular to and intersecting the beam of electromagnetic radiation, thus creating in the output plane of the incident beam a first subset of areas having high intensity relative to a second subset of areas having low intensity. The size of the high intensity areas in the first subset and the size of the low intensity areas in the second subset are selected to be substantially on the same order of magnitude as the size of the element suspected of being present in the receiver. The relative sizes of those areas are determined by several factors, among which are the size of the optical fiber, the radial profile of the index of refraction across the optical fiber, and the manner in which the incident radiation is coupled into the optical fiber. Having generated a beam of incident electromagnetic radiation having a desired spatial distribution of intensity periodically varying with time over distances of the order of magnitude of an element which is sought to be detected or measured, the method and apparatus provide that such periodicity or variation with time of the intensity distribution averages out or masks emitted signals from emitters of electromagnetic radiation present in the receiver which are uniformly distributed or of a size such that they are not responsive to the periodic change of the spatial distribution of intensity.

Figure 2:
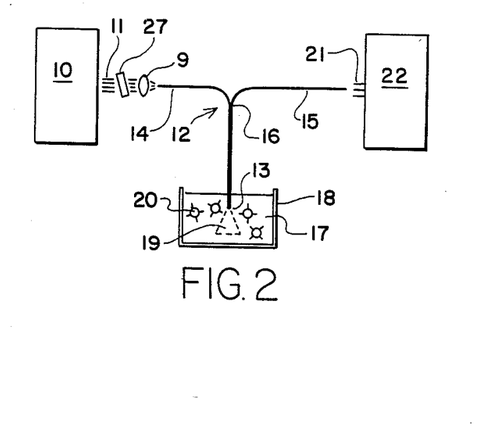
FIG. 2 is a schematic of the apparatus of the present invention.

Turning now to the drawings, as is illustrated with reference to FIG. 2, a light source 10, typically a laser light source, produces a beam of electromagnetic radiation 11 which is incident on the input end of an optical fiber 12 after passing through a focusing lens 9. The beam of electromagnetic radiation passes through a rotatable transparent mass of material 27 which can vary the angle of incidence of the light spectrum on the input end of optical fiber 12. Optical fiber 12 consists of an input fiber 14 and an output or detector fiber 15 which are joined at a junction 16, typically by a Y-coupled. The optical fiber 12 has a probe tip 13 which extends into a sample 17 maintained in a container 18. The incident radiation beam from the tip of the optical fiber defines a sample volume 19, i.e. a receiver, which is substantially cone shaped. Sample 17 typically will contain or be suspected of containing particles 20, i.e. a selected element, which will emit or absorb electromagnetic radiation upon irradiation by the incident beam of electromagnetic radiation. Some of the emitted signal is transmitted through tip 13 into detector fiber 15 to produce an output signal 21 which is picked up by detector 22. The detector is a device capable of receiving photons and converting them to a form which permits differentiation between signals of different intensities. A photomultiplier is a typical example. Detector 22 also includes an autocorrelator instrument, such as that available from Nicomp Instruments, Santa Barbara, Calif., as Computing Autocorrelator, Model No. TC-100, and is utilized to indicate the correlation between fluctuations in the output signal 21 and the periodicity of the intensity distribution of the incident electromagnetic beam.

The volume from which the fluorescent light is obtained is determined by the construction of the optical fiber. The shape of the volume will normally be conical. The optical fibers are typically constructed of a core region and one cladding region, whose diameters and relative refractive indices determine both the half angle of the cone and the cone's smallest diameter (at the tip of the fiber). The effective axial length is determined by the intensity of the excitation beam and the rate of drop in intensity of the excitation light with increasing axial distance from the fiber tip. This rate depends upon the half angle of the cone (i.e. fiber acceptance angle), with larger half angles causing greater rates of intensity drop and hence shorter effective cone lengths. The effective axial length is also determined by the rate of drop of efficiency by which the fiber collects signals from sources further from the fiber. This rate also depends on the fiber acceptance angles. With larger angles the drop of collection efficiency begins at short axial distances. Also affecting the intensity drop will be light scattering and absorption properties of the medium.

The optical fiber employed for producing the effective sample volume will generally have a diameter of about 5 microns to about 500 microns more usually from about 10 microns to 100 microns. The cone half angle of the effective sample volume will generally range from about 8° to about 60°, more usually from about 10° to about 30°. The effective length of the axis will also vary significantly generally ranging from about 0.5 to about 10 fiber diameters, more usually from about 1 to about 5 fiber diameters. The construction of the optical fiber determines the size of the high and low intensity spots in the speckle pattern as does the distance from the end of the optical fiber probe to any particular point in the sample volume. Typically, it is desirable that the size of the spots in the sample volume not vary by more than a factor of two. For example, the speckle pattern from a 50 micron diameter fiber has approximately 150 spots of high intensity and about the same number of low intensity spots. At the tip of the fiber, the approximate diameter of an individual spot is about 2.5 microns, and at the approximate edge of the sample volume (i.e. about 50 microns from the end of the probe) the spot size is about 3.5 microns.

A particularly useful optical fiber device is the commercially available device known as a coupler, consisting of three optical fibers joined at a junction with three terminal ports, conveniently referred to as an input port (into which excitation light is fed), a probe port (which is submerged in the sample) and a detector port. In a form convenient for use in the present invention, the fibers are joined in such a manner that substantially all light entering the input port is transmitted to the probe port. Light entering the probe port (as from the fluorescent emission or elastically scattered light) may be split at the conduit juncture so that a portion will travel to the input port and a second portion to the detector port. Alternatively, a dichroic mirror can be utilized at the juncture directing substantially all of the fluorescent light to the detector port. Such devices are available from commercial suppliers, for example: Kaptron Incorporated, Palo Alto, Calif.

Figure 3:
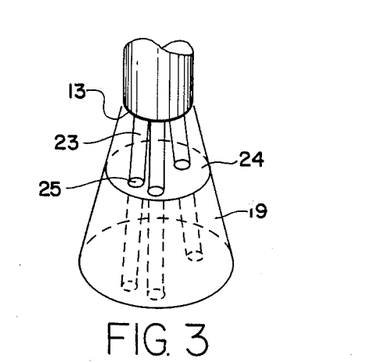
FIG. 3 is a representation of the incident electromagnetic radiation distribution utilized in the present invention.
Figure 4:
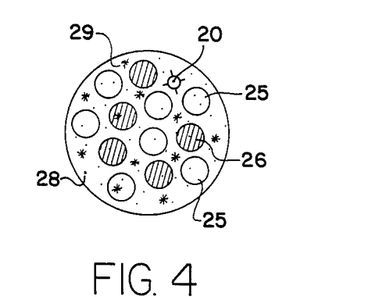
FIG. 4 is a representation of a planar pattern of the incident electromagnetic radiation distribution in a plane intersecting the receiver of the incident radiation at a specific point in time.
Figure 5:
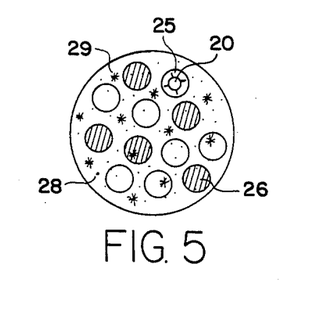
FIG. 5 is a representation of a planar pattern of the incident electromagnetic radiation distribution in the receiver on a plane intersecting the receiver at a different period of time.

As can be seen most clearly in FIG. 3, the output beam from tip 13 of optical fiber 12 produces cones or rays of electromagnetic radiation which define high and low intensity areas on a plane 24 intersecting the sample volume and the output beam of radiation. Reference is made to plane 24 to facilitate understanding of the interaction of the element sought to be detected in the receiver or sample and the intensity distribution of the incident radiation beam. However, it should be clear that signals are generated by an element in the sample volume whether or not the particle would intersect plane 24 as illustrated. At each point in the sample volume, planes parallel to plane 24 can be visualized, which will intersect all particles in the sample volume. The following discussion applies to such planes of intersection as well. As illustrated in FIG. 4, the high intensity areas 25 and low intensity areas 26 are of a size on the same order of magnitude as the dimensions of a particle 20 which is sought to be detected. The more closely the size of the high intensity areas 25 (or the low intensity areas 26) approximates or compares to the size of the element to be measured, the greater the enhancement of detection of a particle is provided. Typically, it is desirable that the mean diameter of the particle is not larger or smaller than the mean diameter of the spot by more than a factor of about 5. FIG. 4 is an illustration of the intensity pattern at a particular point in time in which the particle 20, which is responsive to the incident electromagnetic radiation, is not impinged upon by high intensity area present in the speckle pattern. At that point in time, particle 20 will not be sufficiently excited to generate a large electromagnetic signal. In FIG. 5, the intensity distribution is shown at a different point in time than that of FIG. 4, in which a high intensity portion of the incident beam impinges particle 20 and thus causes particle 20 to emit a larger electromagnetic signal in response to the incidence of such electromagnetic radiation. The emitted electromagnetic signal will be transmitted through output fiber 15 into detector 22 which will indicate a fluctuation in the output electromagnetic signal at that particular instant in time.

In contrast to the effect created by the particle 20 when the spatial distribution is periodically varied, it can be seen from FIGS. 4 and 5 that the uniformly distributed particles 28, such as free molecules exemplified by fluorescent particles which are smaller than the spots, will, on the average, emit approximately the same signal upon irradiation whether or not the spatial distribution of intensity is as depicted in FIG. 4 or FIG. 5. On the average, the same number of particles 28 will be irradiated by high intensity portions of the incident beam and the same number of particles 28 will be irradiated by low intensity portions of the incident beam in either spatial distribution with the effect of generating a signal independent of the periodic change of the spatial distribution. Substantially larger particles will be recognized as substantially uniformly distributed particles and present a similar averaging affect.

Figure 6:
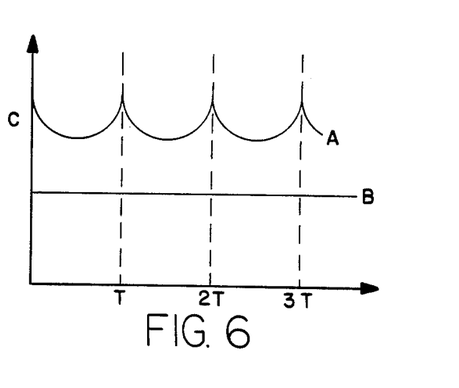
FIG. 6 is a representative plot of the indicated correlation as a function of the periodicity of the incident radiation intensity distribution.

By correlating the fluctuations which are detected or measured by detector 22 with the periods of the changing intensity distribution, it is possible to determine whether or not an element desired to be detected or measured, such as a particle 20, is present in the effective sample volume. As an example, reference can be had to FIG. 6 in which line B indicates no correlation between the periodicity of the intensity distribution and fluctuations in the electromagnetic signal and line A illustrates a high degree of correlation between the periodicity of the varying intensity distribution of the incident beam of electromagnetic radiation and the fluctuations in the measured electromagnetic signal. Since the instrumentation background noise is dependent primarily on the average intensity of the incident beam of radiation, by simply varying the spatial distribution of intensity while at the same time keeping the mean or average intensity over a plane intersecting the sample volume constant, the background or instrumentation noise is not changed. Likewise, emitted electromagnetic radiation from material present in the receiver, such as uniformly distributed elastically scattering or fluorescing tags or particles or objects having cross-sectional dimensions or a mean diameter differing from the cross-sectional dimensions or mean diameter of the high the low intensity areas, will not be influenced by the periodically changing intensity distribution of the incident electromagnetic beam.

The amount of fluorescent light received by the optical fiber from the effective sample volume may be affected by a number of factors. The light scattering of the medium may vary, depending upon the source of the sample, as well as the reagents employed in the assay. Also, various soluble dyes may be present in the continuous aqueous medium, which dyes will absorb light. Filters may also be employed which will cut out light outside of a predetermined wavelength range. In this way, the observed base level may be varied widely in accordance with the requirements of the assay.

The excitation light may be provided by irradiating the entire sample or a major portion of the sample with excitation light. Alternatively and preferably the excitation light may be provided by the optical fiber, so that the sample volume observed will be proportional to the volume irradiated.

When the method and apparatus described are utilized to irradiate a receiver suspected of containing a selected element responsive to irradiation by emitting an electromagnetic signal, the signal from the selected element can be detected and measured in an enhanced manner relative to the background radiation. The selected element can comprise diverse entities depending on the measurement system in question. For example, the element can be a particle which fluoresces or elastically scatters light in response to incident radiation. It may be a particle which absorbs an incident radiation such that the presence of the particle is detected by a negative fluctuation from a base value for the overall electromagnetic signal emitted. As a further example, the element or object may be an entity having a characteristic causing it to emit a greater signal than the same entity not having the particular characteristic (e.g. a cell having an abnormality which causes it to emit a larger or more powerful signal than that same cell not having the abnormality).

The subject invention has particular application for determining an analyte in a sample, where the amount of analyte affects an observed pattern of fluorescence fluctuations. The analyte is a member of a specific binding pair consisting of ligand and its homologous receptor. The optical fiber is employed to receive fluorescent light from the sample volume. One observes a plurality of such volumes, either by observing a single volume over an extended period of time, where particles move in and out of the volume, or scanning a plurality of volumes either simultaneously or successively, or combinations thereof. Thus, the percentage of volumes observed which have a predetermined difference in fluorescence from a defined level can be related to the amount of analyte in the medium.

The fluctuations in fluorescence can be achieved by various combinations of particles and continuous media. For example, the combinations can include particles which fluoresce at constant intensity in a non-fluorescing solution, particles which fluoresce at varying intensity in a non-fluorescing solution, particles which are non-fluorescent in a fluorescent solution and fluorescent particles in a fluorescent solution. Furthermore, the fluorescent fluctuation may be a result of aggregation of particles, non-fluorescent particles becoming fluorescent, or fluorescent particles becoming non-fluorescent. The particles may be comprised of polymers, both naturally occurring or synthetic, natural particles, such as virions and cells, e.g., blood cells and bacteria, or the like. Particle sizes will vary from 0.05 to 100, where synthetic particles will generally be from about 0.1 to 10 diameter.

By employing the above-described method in a fluorescent assay, a large number of protocols and reagents may be employed. On group of protocols will involve measuring fluorescent particles. This group can be further divided into particles which remain uniformly fluorescent, that is, there are basically two particle populations, fluorescent or non-fluorescent, where fluorescence above a certain level is defined as a positive or negative result. The invention has been found to be particularly advantageous in protocols in which a fluorescing molecule is conjugated directly to an antibody (Ab), which then binds directly to a cell.

In one application to be described, the particles may be uniformly fluorescent. As a result of binding of a quencher label to a particle, the particle becomes non-fluorescent. For example, fluorescent particles can be prepared having a ligand bound to the particles, which ligand is an analog of the analyte. Charcoal particles can be conjugated with anti-ligand (a receptor which specifically binds to a ligand). By combining in an assay medium, the sample containing the analyte, the ligand conjugated fluorescent particle and the anti-ligand conjugated charcoal particles, the number of charcoal particles which bind to the fluorescent particles over a predetermined time period will be determined by the amount of analyte in the medium. Thus, at time $t_1$ one examines a number of sample volumes and determines what percentage of these sample volumes results in the fluorescence being greater than the threshold value. After an interval of time, at time $t_2$, one repeats the same measurement. The rate of change in the percentage of sample volumes being greater than the threshold value will be related to the amount of analyte in the medium. This analysis has assumed that the binding of a charcoal particle to a fluorescent particle through the intermediacy of non-covalent binding of the ligand and the anti-ligand results in complete or substantially complete quenching of the fluorescent particles. Where only a small percentage of the total fluorescence is quenched by a charcoal particle, then the analysis will be basically the same as a heterogeneous population of particles having varying fluorescence.

A heterogeneous population of fluorescent particles can come about in a number of ways. For example, one can have aggregation or agglutination of particles. The analyte could be a receptor or antibody, which is polyvalent in binding sites. Fluorescent particles could be conjugated with ligand, so that the polyvalent receptor would act as a bridge between particles. In this way, the greater the amount of analyte present in the medium, the larger the number of aggregates which will result. The particle of interest could then be chosen as a particle which is an aggregation of two or more or three or more particles. Furthermore, by appropriate electronic means, one could determine the size of the aggregation, counting not only the total number of particles, but the number of members of each population. As the aggregation increases in size, the fluorescence of the aggregate particle will also increase, but not linearly with the increase in the number of particles in the aggregation.

A second way for having a heterogeneous population has in part already been considered, where binding of quencher to a fluorescent particle only partially diminishes fluorescence. Alternatively, one could have a non-fluorescent particle, where fluorescent molecules become bound to the particle in proportion to the amount of analyte in the medium or to the number of binding sites on the particle. For example, one could have fluorescent molecules bound to an antiligand. Ligand could be bound to a non-fluorescent particle. The fluorescer conjugated antiligand would be combined with the analyte containing sample, so that the analyte could fill the binding sites of the antiligand, with the remaining binding sites being related to the amount of analyte in the sample. Upon addition of the ligand conjugated particles to the medium, the remaining fluorescent conjugated receptor would bind to the particles, providing for a distribution of particles of varying fluorescence.

A third technique may also be illustrated by employing an aggregation. In this technique, non-fluoresent particles are employed, and the continuous phase is made fluorescent. Thus, when the aggregation is present in the sample volume, there will be a substantial diminution in the observed fluorescence. These particles, while non-fluorescent should also be substantially opaque to excitation of fluorescent light. Thus, they will create a substantial shadow, inhibiting the detection of fluoresce in a volume substantially greater than the volume of the aggregation.

A fourth way of obtaining a heterogeneous population of fluorescent particles is to allow a fluorescent tag to label non-fluorescent particles. For example, non-fluorescent particles may be cells which have a plurality of antigens on the cell surface, there being a number of each antigen present. By employing fluorescer-labeled-antibodies to specific surface antigens, a specific set of non-fluorescent cells will become fluorescent. The detection of the presence of such cells is a preferred method of cell identification, e.g. red blood cell (RBC) grouping and typing. For example, in the A, B, O system, if the fluorescent tag were conjugated to anti-A antibody, binding would occur and there would be a greater increase in cell fluorescence if the sample contained the A antigen of type A or type AB blood than if the analyte contained blood types B or O.

In addition to antibodies, certain lectins are known to bind in varying degrees to RBC surface antigens, and are convenient receptors for use in fluorometric assays.

Usually, there will be a distribution of levels of fluorescence, although in some situations it will be feasible to substantially saturate the available binding sites on the cell surface, so as to approximate only two populations, non-fluorescent cells and cells of substantially uniform fluorescence.

While not presently preferred, typing red blood cells (RBCs) or identifying red blood cell (RBC) antigens or the antibodies thereto can be effective by using the RBCs as fluorescence quenchers in an assay employing fluorescent particles to provide a detectable signal. Substances which bind to RBC antigens, normally antibodies or lectins (hereinafter "receptors") are conjugated to fluorescent particles. A solution of particle-conjugates is combined with red blood cells, e.g., whole blood, with an appropriate buffer. If an antigen is present on the RBCs that has a binding or determine site specific for the receptor, the conjugated particles will bind to the RBCs which act as fluorescence quenchers.

Also, the determination of the presence of antibodies to a RBC antigen can be made. Three different techniques may be used. In one, fluorescently labeled antibody compete with antibodies in the plasma or serum sample for antigen sites on test RBCs of a known group, with the observed cellular fluorescence decreasing with increasing amounts of antibodies against the specific antigen in the sample. Alternatively, the test RBCs may be fluorescently stained and, when combined with serum, the specific antibodies, if present, will agglutinate the fluorescent cells. In a third method, the fluorescent bead may be conjugated with the surface antigen of interest and antibodies present in the sample act as a bridge between RBCs of known type and the antigen conjugated fluorescent particles. In this situation, decreasing fluorescence would indicate the presence of the antibodies.

High extinction coefficients for the fluorescer are desirable and should be greatly in excess of 10,000 cm$^{-1}$ M$^{-1}$ and preferably in excess of 100,000 cm$^{-1}$ M$^{-1}$. The fluorescer should also have a high quantum yield, preferably between 0.3 and 1.0.

In addition, it is desirable that the fluorescer have a large Stokes shift, preferably greater than 20 nm, more preferably greater than 30 nm. That is, it is preferred that the fluorescer have a substantial spread or difference in wavelengths between the absorption and emission maxima.

One group of fluorescers having a number of the desirable properties are the xanthene dyes, which include the fluoresceins derived from 3,6-dihydroxy-9-phenylxanthhydrol and rosamines and rhodamines, derived from 3,6-diamino-9-phenylxanthene. The rhodamines and fluoresceins have a 9-0-carboxyphenyl group, and are derivatives of 9-0-carboxy-phenylxanthene.

These compounds are commercially available with or without substituents on the phenyl group.

Another group of fluorescent compounds are the naphthylamines, having an amino group in the alpha or beta position, usually alpha position. Included among the naphthylamino compounds are 1-dimethylaminonaphthyl-5-sulfonate, 1-anilino-8-naphthalene sulfonate and 2-p-toluidinyl-6-naphthalene sulfonate. Other fluorescers of interest include coumarins, e.g., umbelliferone, and rare earth chelates, e.g., Tb, Eu, etc. Descriptions of fluorescers can be found in Brand, et al., *Ann. Rev. Biochem.* 41, 843–868 (1972) and Stryer, *Science*, 162, 526 (1968).

Appropriate particles are combined with the fluorescer using standard techniques to provide fluorescent beads or microspheres. Fluorescent particles are commercially available. The fluorescent beads may be varied widely as to size and composition. The beads will normally be made of an inert material and include a plurality of fluorescent chromophoric functionalities. The beads will have a sufficient concentration of fluorescent functionalities to provide for a large signal per bead. Various organic polymers may be employed for the bead, e.g., polystryrene, polymethacrylate or the like or inorganic polymers, e.g., glass or combinations thereof. The particular choice of the polymeric composition is primarily one of convenience.

Conjugated to the fluorescent beads either covalently or non-covalently are receptors which may be antibodies, including monoclonal antibodies, or lectins, that bind either specifically or differentially to specific RBC surface antigens or antigens having the determinant site(s) of such RBC surface antigens or other antigens of interest.

The receptors are adsorbed to the fluorescent bead using standard techniques extensively described in the literature, which need not be repeated here. Alternatively, the receptors may be covalently bound by conventional techniques.

In one example of an assay, an RBC sample in a buffered aqueous solution comprising from 1–50% RBCs by volume is mixed with an approximately equal volume of the conjugated fluorescent receptor solution. As a control, an identical volume of fluorescent-Ab solution may be mixed with an equal volume of RBCs that lack specificity to the Ab. The mixed solutions are allowed to stand for up to 120 min., preferably 1–10 minutes at mild temperatures from above 0° C. to about 37° C., preferably about 15°–25° C. Other controls may be used. Free antigen or antibody could be added as an example, or the result could be compared with standard preparations of Type A, B or O blood or serum.

Results of various correlation studies utilizing the above described method and apparatus are described in the following examples which are intended to illustrate but not limit the present invention.

EXAMPLE 1

This example was conducted with a fluid sample containing no fluorescent particles to demonstrate that the background radiation resulting from the leakage of excitation light and resulting from electromagnetic signals generated within the measurement and detection apparatus does not correlate with the periodicity of a periodically varying spatial intensity distribution of incident radiation on the sample.

Filtered water was placed in a 2.0 ml. sample container. The single fiber end of a "Y"-shaped fiber optics coupler obtained from Kaptron, Inc., Palo Alto, Calif. (Fiber Optic Wavelength Multiplexer, Model FOWM-1-2) was submerged in the fluid. The fiber core had a diameter of 50 microns and produced an excitation cone with a half angle of 12° and an effective sampling volume of about $1 \times 10^{-7}$ ml. The speckle pattern on an output plane in the sample has approximately 150 spots of high intentisty and about 150 spots of low intensity. At the tip of the fiber, the approximate diameter of an individual spot was about 2.5 m and at a depth of about 50 m into the sample had increased to about 3.5 m. Excitation light from a He-Cd laser was fed into the input branch fiber of the optical fiber. The detector branch of the optical fiber was coupled to a photomultiplier and preamplifier discriminator. The output signal from the preamplifier discriminator was interfaced with an autocorrelator (Computing Autocorrelator, Model No. TC-100, obtained from Nicomp Instruments, Santa Barbara, Calif.). A cam was positioned in contact with a portion of the input branch of the optical fiber, and connected to a motor for rotation at 33 cycles per second. The channel width of the autocorrelator was set at 2 milliseconds and the signal was prescaled so as not to saturate the counters in the autocorrelator. The autocorrelator output was observed as the cam was rotated to periodically change the position of the input branch of the optical fiber. The output as a function of time was flat, indicating no correlation between the period of change of the spatial distribution of intensity of the incident radiation and the component of background radiation created by excitation light leakage and generated by the instrumentation.

EXAMPLE 2

This example was conducted with a fluid sample containing a uniformly distributed fluorescer by diluting 1 part of a $1 \times 10^{-5}$M fluorescein solution with 1000 parts of the filtered water as employed in Example 1. The apparatus was identical to that described in Example 1 and the output of the autocorrelator as a function of time was flat, demonstrating the absence of correlation between the periodicity and the component of background radiation due to fluorescence independent of the particle to be detected.

EXAMPLE 3

The fluid sample utilized in Example 2 was combined with 100 l of a solution containing $3 \times 10^7$ untagged red blood cells/ml. and the method and apparatus described in Example 1 were utilized. Observation of the autocorrelator output as a function of time indicated the absence of correlation between the measured signal and the period of change of the spatial distribution of intensity of the incident beam with time.

EXAMPLE 4

10 l of a solution containing $10^6$, 1.5 m diameter fluorescent beads (Fluoresbrite -fluorescent monodisperse carboxylated microspheres, Catalog No. 9719, Polysciences, Inc., Warrington, Pa.) was added to the fluid sample of Example 3. The method and aparatus of Example 1 were utilized. Observation of the output of the autocorrelator as a function of time demonstrated a definite observable correlation between the fluctuation in the measured signal and the period of change of the spatial distribution of intensity of the incident beam with time.

EXAMPLE 5

A 0.5 cm. diameter, 1 mm. thick glass flat cemented to the shaft of an optical scanner (Model No. G-100 PD, General Scanning Inc., Watertown, Md.) was connected to an electronic driver (Model No. CCX-651, General Scanning, Inc.) and set to rotate the glass flat (corresponding to Reference Numeral 27 in FIG. 2 of the drawings) 15° about the position normal to the laser beam (Argon laser at 488 nanometers). Rotation of the glass flat results in a slight translation of the incident laser beam with all beam rays parallel to each other. The glass flat was driven at a rate of 300 cycles per second.

A $5 \times$ microscope objective was utilized as a short focal length lens (corresponding to Reference Numeral 9 in FIG. 2) to focus the incident laser beam on the input end of the optical fiber. A bifurcated fiber optic bundle (Bundle No. 831150, Maxlight Fiber Optic Division of Raychem, Corp., Phoenix, Az.) was utilized for the optical fiber and consisted of one input fiber, as the central fiber in the bundle, surrounded by six output fibers which formed the detector branch of the optical fiber bundle. The input and output branches were formed to present substantially zero cross-talk between the two branches and the sample volume was defined by the intersection of the conical volume in front of the central fiber and the conical volumes of the six detector fibers, resulting in a sample volume about 10 times larger than that obtained from the single 50 mm fiber. The detector apparatus as described in Example 1 was utilized except that the correlator channel width was set to 0.2 ms.

The solution of fluorescent beads described in Example 4 and the method described in Example 1 were utilized. Observation of the output of the autocorrelator as a function of time demonstrated a definite observable correlation between the fluctuation in the measured signal and the period of change of the spatial distribution of intensity of the incident beam with time.

The foregoing procedure was repeated with a sample of free fluoroscein and no correlation was detachable.

While the foregoing invention has been described with reference to the drawings and the examples, and the presently preferred embodiments, they are intended to be illustrative and not intended to limit the scope of the invention herein claimed. Various modifications or changes to the methods and apparatus described herein will be apparent to those skilled in the art and are intended to be included and encompassed by the claims appended hereto.

What is claimed is:

1. A method of detecting fluctuations in an electromagnetic signal emitted by a receiver of incident electromagnetic radiation in response thereto, said receiver suspected of containing an element to be detected and/or measured, which comprises:

generating a beam of incident electromagnetic radiation having a spatial distribution of intensity periodically varying in time; irradiating at least a portion of said receiver with said beam; measuring the electromagnetic signal emitted by at least a portion of said irradiated receiver; and determining the correlation, if any, between the periodicity of said periodically varying spatial intensity distribution and fluctuations in said measured signal.

2. The method of claim 1 wherein said spatial distribution of intensity defines a plurality of substantially discrete areas of differing intensity in a plane intersecting said beam, a first subset of said areas having a high intensity relative to a second subset of said areas, the size of said areas in said subsets being of the same order of magnitude as the size of said element.

3. The method of claim 2 wherein said size of said areas is defined by a mean diameter which is substantially comparable to the mean diameter of said element suspected of being in said receiver.

4. The method of claim 1 wherein said emitted electromagnetic signal includes elastically scattered light.

5. The method of claim 1 wherein said emitted electromagnetic signal includes inelastically scattered light.

6. The method of claim 1 wherein said beam is generated from a coherent light source.

7. The method of claim 6 wherein said beam is generated utilizing wave-front interference.

8. The method of claim 1 wherein said beam includes a wavelength within the visible spectrum.

9. A method for determining the presence of an analyte in a sample suspected of containing said analyte which comprises;

combining said sample with a source of fluorescence;

forming a set of excitation light rays including a first subset of light rays having a net amount of constructive interference and a second subset of light rays having a net amount of destructive interference, said first and second subsets having an initially determined spatial distribution relative to each other;

irradiating said combined sample and source with said set of excitation light rays;

periodically changing the relative spatial distribution of said first and second subsets of light rays during said irradiation; and determining the correlation, if any, between the measured fluctuations of fluorescent intensity from said combined sample and source and said periodicity.

10. The method of claim 9 wherein said combined sample and source includes a particle containing assay medium and the mean diameter of said excitation rays is of the same order of magnitude as the mean diameter of said particles.

11. The method of claim 9 wherein said set of excitation light rays is formed by transmitting a coherent light source through an optical fiber light guide.

12. The method of claim 11 wherein the periodic change in the spatial distribution of said first and second subsets of light is effected by changing the path of radiation from said coherent light source through said optical fiber light guide.

13. A method of determining the presence of an analyte in a sample suspected of containing said analyte which comprises:

combining said sample with a source of fluorescence;

irradiating said combined sample with a radiation source spectrum sufficiently narrow to permit radiation guided in different modes to interfere at an output plane intersecting a portion of said combined sample;

periodically changing the path of the guided radiation to vary the interference pattern at said output plane during said irradiation; and determining the correlation, if any, between the measured fluctuations of fluorescent intensity from said combined sample and said periodic change.

14. The method of claim 13 wherein said fluorescent source includes a particle containing assay medium and at least one of said particles is fluorescent or said medium contains a fluorescer.

15. The method of claim 13 wherein said measured fluctuations are a result the aggregation of particles.

16. The method of claim 15 wherein said particles are fluorescent.

17. The method of claim 14 wherein said measured fluctuations are a result of binding of a fluorescer to a non-fluorescent particle.

18. The method of claim 14 wherein said measured fluctuations are a result of quenching of the fluorescence of a fluorescent particle.

19. The method of claim 13 wherein said source spectrum is a coherent light source.

20. The method of claim 19 wherein an optical fiber is utilized to transmit said coherent light to and irradiate said combined sample and source.

21. An apparatus for detecting fluctuations in electromagnetic signal emitted by a receiver of incident electromagnetic radiation in response thereto which comprises:

means for generating a beam of incident electromagnetic radiation having a spatial distribution of intensity periodically varying in time;

means for irradiating a receiver with said beam;

means for measuring an electromagnetic signal emitted by said receiver upon irradiation;

means for determining the correlation, if any, between the periodicity of said periodically varying spatial intensity distribution and fluctuations in said measured signal.

22. The apparatus of claim 21 wherein said generation means includes of a source of coherent radiation.

23. The apparatus of claim 22 wherein said generation means includes an optical fiber adapted to receive radiation from said source.

24. The apparatus of claim 23 wherein said generation means includes means periodically changing the spatial position of a portion of said optical fiber.

25. The apparatus of claim 24 wherein said position changing means includes a rotatable cam adapted to contact a portion of said optical fiber.

26. The apparatus of claim 23 including means associated with said source and said optical fiber operable to periodically change the angle of incidence of radiation from said source onto said optical fiber.

27. The apparatus of claim 26 wherein said associated means comprises a rotatable mass adapted to transmit and refract radiation incident thereon.

28. An apparatus for measuring light from a fluid sample comprising:

an optical light guide having a probe adapted to extend into said fluid sample, said probe having an input light guide and a detector light guide;

light irradiating means optically coupled to said input light guide;

light detection means optically coupled to said detector light guide;

modulating means operable on said input light guide to form excitation light means having a time dependent spatial intensity distribution pattern including contrasting areas of high intensity and low intensity;

means for measuring an emitted signal from said fluid sample in response to said excitation light; and means for determining the correlation, if any, between the period of said modulation and the fluctuations in the measured signal.

29. The apparatus of claim 28 wherein the optical light guide is an optical fiber.

30. The apparatus of claim 29 wherein the light irradiating means is a laser light source.

* * * * *